United States Patent
Robinson (10) Patent No.: US 11,135,046 B2
(45) Date of Patent: Oct. 5, 2021

(54) ANIMAL SPLINT

(71) Applicant: Wheels for Pets, LLC, Amherst, NH (US)

(72) Inventor: Mark C. Robinson, Amherst, NH (US)

(73) Assignee: WHEELS FOR PETS, LLC, Amherst, NH (US)

( * ) Notice: Subject to any disclaimer, the term of this patent is extended or adjusted under 35 U.S.C. 154(b) by 1027 days.

(21) Appl. No.: 15/268,759

(22) Filed: Sep. 19, 2016

(65) Prior Publication Data
US 2018/0078352 A1 Mar. 22, 2018

(51) Int. Cl.
*A61D 3/00* (2006.01)
*A61D 9/00* (2006.01)
(Continued)

(52) U.S. Cl.
CPC .................. *A61D 3/00* (2013.01); *A61D 9/00* (2013.01); *A61D 2003/006* (2013.01);
(Continued)

(58) Field of Classification Search
CPC ........ A61F 5/01; A61F 5/0102; A61F 5/0104; A61F 5/0106; A61F 5/0109; A61F 5/0111; A61F 5/0113; A61F 5/0123; A61F 5/0125; A61F 5/0127; A61F 5/013; A61F 5/058; A61F 5/05825; A61F 5/05841; A61F 5/0585; A61F 5/05858; A61F 2005/0132; A61F 2005/0137; A61F 2005/0139; A61F 2005/0144; A61F 2005/0146; A61F 2005/0155; A61F 2005/0158; A61F 2005/016; A61F 2005/0165;
(Continued)

(56) References Cited

U.S. PATENT DOCUMENTS 2,312,523 A 3/1943 Corbett
2,333,033 A 10/1943 Mraz
(Continued)

FOREIGN PATENT DOCUMENTS

FR 2810198 A1 12/2001
GB 561634 5/1944
(Continued)

OTHER PUBLICATIONS

PCT search report for counterpart PCT Appl. No. PCT/US2017/052230, dated Feb. 9, 2018.
(Continued)

*Primary Examiner* — Rachael E Bredefeld
*Assistant Examiner* — Rachel A Berezik
(74) *Attorney, Agent, or Firm* — Robert Deleault; Sarita Pickett (57) ABSTRACT

An animal splint for immobilizing a leg of an animal receives the back and sides of the injured leg and is angularly adjustable to the normal angle of the upper and lower part of the injured leg prior to sustaining the leg injury. The splint includes a lower leg assembly, an upper leg assembly, an adjustment member configured for setting the angle between the lower leg assembly and the upper leg assembly, and a leg retaining means that extends across the lower leg open front and the upper leg open front where the lower leg assembly and the upper leg assembly receives the back and sides of the injured leg.

11 Claims, 9 Drawing Sheets

(51) Int. Cl.
*A61F 5/01* (2006.01)
*A61F 5/058* (2006.01)

(52) U.S. Cl.
CPC ............... *A61F 5/01* (2013.01); *A61F 5/058* (2013.01); *A61F 5/05841* (2013.01)

(58) Field of Classification Search
CPC .............. A61F 2005/0167; A61D 3/00; A61D 2003/006; A61D 9/00; A01K 13/00; A01K 13/006; A01K 13/007; A01K 15/04
See application file for complete search history.

(56) References Cited

U.S. PATENT DOCUMENTS

| | | | |
|---|---|---|---|
| 3,416,519 A | 12/1968 | Dowers | |
| 3,470,873 A | 10/1969 | Walker et al. | |
| 3,680,552 A | 8/1972 | Bell et al. | |
| 4,029,090 A | 6/1977 | Dawson, Jr. | |
| 4,361,143 A | 11/1982 | Nelson | |
| 4,524,764 A | 6/1985 | Miller | |
| 4,611,586 A | 9/1986 | Agee et al. | |
| 4,612,925 A | 9/1986 | Bender | |
| 4,922,896 A | 5/1990 | Agee et al. | |
| 5,134,992 A | 8/1992 | Campbell | |
| 5,836,902 A | 11/1998 | Gray | |
| 5,873,847 A | 2/1999 | Bennett et al. | |
| 5,925,005 A | 7/1999 | May | |
| 6,042,557 A | 3/2000 | Ferguson et al. | |
| 6,179,798 B1 | 1/2001 | Nelson | |
| 6,203,511 B1 * | 3/2001 | Johnson | A61F 5/0125 602/16 |
| 6,517,504 B1 * | 2/2003 | Postelmans | A61F 5/0123 602/26 |
| 6,572,571 B2 | 6/2003 | Lowe | |
| 7,662,117 B2 | 2/2010 | Parizot | |
| 9,408,738 B2 * | 8/2016 | Boraas | A61F 5/01 |
| 2001/0026135 A1 | 10/2001 | Zalkin et al. | |
| 2002/0072695 A1 * | 6/2002 | Doty | A61F 5/0125 602/5 |
| 2004/0255955 A1 | 12/2004 | Daly | |
| 2006/0004310 A1 | 1/2006 | Parizot | |
| 2006/0079819 A1 | 4/2006 | Evans et al. | |
| 2006/0155230 A1 * | 7/2006 | Mason | A61F 5/0125 602/16 |
| 2007/0156070 A1 | 7/2007 | Schwab | |
| 2007/0191749 A1 | 8/2007 | Barberio | |
| 2008/0262400 A1 | 10/2008 | Clark et al. | |
| 2010/0022929 A1 * | 1/2010 | Pansiera | A61F 5/0123 602/16 |
| 2010/0191162 A1 | 7/2010 | Chang et al. | |
| 2016/0367392 A1 * | 12/2016 | Pflaster | A61F 5/01 |

FOREIGN PATENT DOCUMENTS

| | | |
|---|---|---|
| GB | 786073 | 11/1957 |
| JP | 1990109613 U | 9/1990 |
| WO | 2016/142319 A1 | 9/2016 |

OTHER PUBLICATIONS

CN Office Action with English translation in co-pending application CN 201780057746.8, dated Aug. 5, 2020.
JP Office Action in co-pending application JP 2019-537020, dated Jul. 14, 2021.
CN 2nd Office Action with English translation in co-pending application CN 201780057746.8, dated Mar. 23, 2021, receipt date Apr. 27, 2021.

* cited by examiner

ANIMAL SPLINT

BACKGROUND OF THE INVENTION

1. Field of the Invention

The present invention relates generally to splints. Particularly, the present invention relates to an adjustable splint suitable for immobilizing the leg of an animal.

2. Description of the Prior Art

Animals frequently suffer orthopedic injuries such as torn ligaments, torn tendons, broken bones, and the like. The use splints or casts to immobilize the limbs of both humans and animals has become a well-established practice. Immobilization speeds recovery and prevents further injury. There has been devised all kinds and shapes of splint devices for various injuries and various animals in veterinary orthopedic medicine.

In order to immobilize a leg, it has been necessary to construct a shaped splint or cast for each leg to be treated. This procedure is time consuming and limits both the ability of an underlying bandage to breath and the ability of the doctor to view either the wound or the bandage. Some solutions tend to be narrowly tailored to fit a specific animal or size of animal. Other solutions are so broad in their intended applications that they tend to not fit any type of animal correctly. Poor fitting and difficulty in use in a practical scenario discourages use of the entire solution. Some solutions are not sufficiently adjustable and, thus, do not remain satisfactorily in place when the animal begins to frequently move about.

These difficulties have been overcome in part by the following devices. U.S. Pat. No. 3,881,472 (1971; Lee) discloses a splint formed of an integral plastic member that is generally semi-cylindrical in cross-section and lined along its interior surface with a soft, resilient material. The area of the splint that receives the paw is ventrally turned so as to place the carpal or wrist joint in a normal resting position.

U.S. Pat. No. 4,361,143 (1982, Nelson) discloses a splint for a hind leg of an animal. The splint is of one-piece construction and shaped to conform to the normal shape of the hind leg. It is formed of rigid, non-flexible material to prevent movement of the injured part of the leg. The splint is curved or C-shaped in cross-section and adequate to receive approximately one side of the leg.

U.S. Pat. No. 5,134,992 (1992, Campbell) discloses an animal splint that is a rigid, elongated member. It has a first section that terminates in a proximal end and a second section that terminates in a distal end. The proximal end is the end closest to the point at which the leg is attached to the body. The distal end is the end furthest from the point of attachment. The splint also has a plurality of holes distributed throughout the rigid, elongated member. The holes provide ventilation and help to prevent the splint from slipping with respect to the bandage when the splint is applied over a bandage.

U.S. Pat. No. 6,179,798 (2001, Nelson) discloses an adjustable splint assembly for use in immobilizing the leg of an animal. The splint assembly includes an elongated sleeve portion having a plurality of taping clips extending outwardly from opposing sides and a shaft portion slidably received with the sleeve portion such that the shaft portion and the sleeve portion are telescopically adjustable. This particular splint is intended to be used over a bandaged leg and provides a rigid rib that is narrower than the width of the leg. It is intended to be placed along the outside of a bandaged leg and then tied to the bandage leg.

SUMMARY OF THE INVENTION

Each of the prior art disclosed above suffers from certain and various disadvantages. These disadvantages include the inability to adjust the angle of the splint to the normal angle between an upper leg and a lower leg of a four-legged animal, the failure to support and protect the back and both sides of the injured leg with a rigid material, and the lack of a foot/paw support as an integral part of the splint.

It is an object of the present invention to provide an animal splint that supports and protects the back and both sides of the injured leg of a four-legged animal and to be capable of adjusting the angle between an upper leg portion and a lower leg portion of the splint.

The present invention achieves these and other objectives by providing an animal splint for immobilizing a leg of an animal that receives the back and sides of the injured leg. It is angularly adjustable to the normal angle formed between the upper and lower parts of the leg based on the animal type and size.

In one embodiment of the present invention, the animal splint includes a lower leg assembly, an upper leg assembly, an adjustment member configured for setting the angle between the lower leg assembly and the upper leg assembly, and a leg retaining means that extends across the lower leg open front and the upper leg open front where the lower leg assembly and the upper leg assembly receives the back and sides of the injured leg.

In another embodiment, the lower leg assembly has a lower leg elongated body with a pair of lower leg opposed sides, a back side, a distal foot support portion, and a lower leg open front forming a lower leg trough-like space. The upper leg assembly has an upper leg elongated body with a pair of upper leg opposed sides, an upper back side, and an upper leg open front forming an upper leg trough-like space.

In a further embodiment, the lower leg assembly has a proximal lower leg portion opposite the distal foot support portion where a cross-sectional area of the lower leg trough-like space at the distal foot support portion is larger than the cross-sectional area of the lower leg trough-like space at the proximal lower leg portion.

In still another embodiment, the upper leg assembly has a distal upper leg portion and a proximal upper leg portion opposite the distal upper leg portion where a cross-sectional area of the upper leg trough-like space at the distal upper leg portion is larger than the cross-sectional area of the upper leg trough-like space at the proximal upper leg portion and where the cross-sectional area of the proximal upper leg portion is generally equal to the cross-sectional area of the proximal lower leg portion.

In yet another embodiment, the proximal lower leg portion of the lower leg assembly has a first angle fixing member integrally formed into at least one of the pair of lower leg opposed sides. The proximal upper leg portion of the upper leg assembly has a second angle fixing member integrally formed into at least one of the pair of upper leg opposed sides and configured for mating engagement with the first angle fixing member of the proximal lower leg portion. The combination of the second angle fixing member and the first angle fixing member permits angular adjustment between the lower leg assembly and the upper leg assembly. The adjustment member is configured for fixing and/or releasing the second angle fixing member of the upper leg assembly and the first angle fixing member of the lower leg assembly relative to each other. The adjustment member permits adjusting an angle between the lower leg assembly and the upper leg assembly to match the angle typical for the type and size of leg.

In another embodiment of the present invention, the lower leg assembly is longer than the upper leg assembly.

In another embodiment of the present invention, the first angle fixing member is a gear-like recess and the second angle fixing member is a gear-like protrusion.

In a further embodiment of the present invention, the leg retaining means is a plurality of leg retaining straps connected to the lower leg assembly and the upper leg assembly whereby some of the plurality of leg retaining straps extends across the lower leg open front between the pair of lower leg opposed sides and some of the plurality of leg retaining straps extends across the upper leg open front between the pair of upper leg opposed sides.

In another embodiment of the present invention, the lower leg assembly includes a first lower leg member having a first lower leg side and a first lower back side portion, and a second lower leg member having a second lower leg side and a second lower back side portion.

In still another embodiment, the upper leg assembly includes a first upper leg member having a first upper leg side and a first upper back side portion, and a second upper leg member having a second upper leg side and a second upper back side portion.

In yet another embodiment of the present invention, the animal splint includes at least one lower leg fastener part configured to retain the first lower leg member to the second lower leg member at a lower leg outside surface opposite the lower leg open front.

In another embodiment, the animal splint includes at least one upper leg fastener part configured to retain the first upper leg member to the second upper leg member at an upper leg outside surface opposite the upper leg open front.

In another embodiment, the at least one lower leg fastener part includes a first lower fastener bracket disposed on the first lower leg member, a second lower fastener bracket disposed on the second lower leg member and a fastener connecting the first lower fastener bracket to the second lower fastener bracket.

In a further embodiment of the present invention, the at least one upper leg fastener part includes a first upper fastener bracket disposed on the first upper leg member, a second upper fastener bracket disposed on the second upper leg member and a fastener connecting the first upper fastener bracket to the second upper fastener bracket.

In another embodiment, there is disclosed a method of using the animal splint of the present invention. The method includes assembling the first angle fixing member of the lower leg assembly and the second angle fixing member of the upper leg assembly to each other at an angle defined by the animal's leg to be immobilized, attaching and tightening the adjustment member to lock the angle between the lower leg assembly and the upper leg assembly, inserting a lower leg of the animal within the lower leg trough-like space of the lower leg assembly, inserting an upper leg of the animal within the upper leg trough-like space of the upper leg assembly, and securing the animal splint on the leg of the animal using the leg retaining means.

In another embodiment of the method of the present invention, the method includes assembling a first lower leg member to a second lower leg member before assembling the first fixing angle member and the second fixing angle member to each other.

In another embodiment of the method, the method includes assembling a first upper leg member to a second upper leg member before assembling the first fixing angle member and the second fixing angle member to each other.

DETAILED DESCRIPTION OF ONE EMBODIMENT

Figure 1:
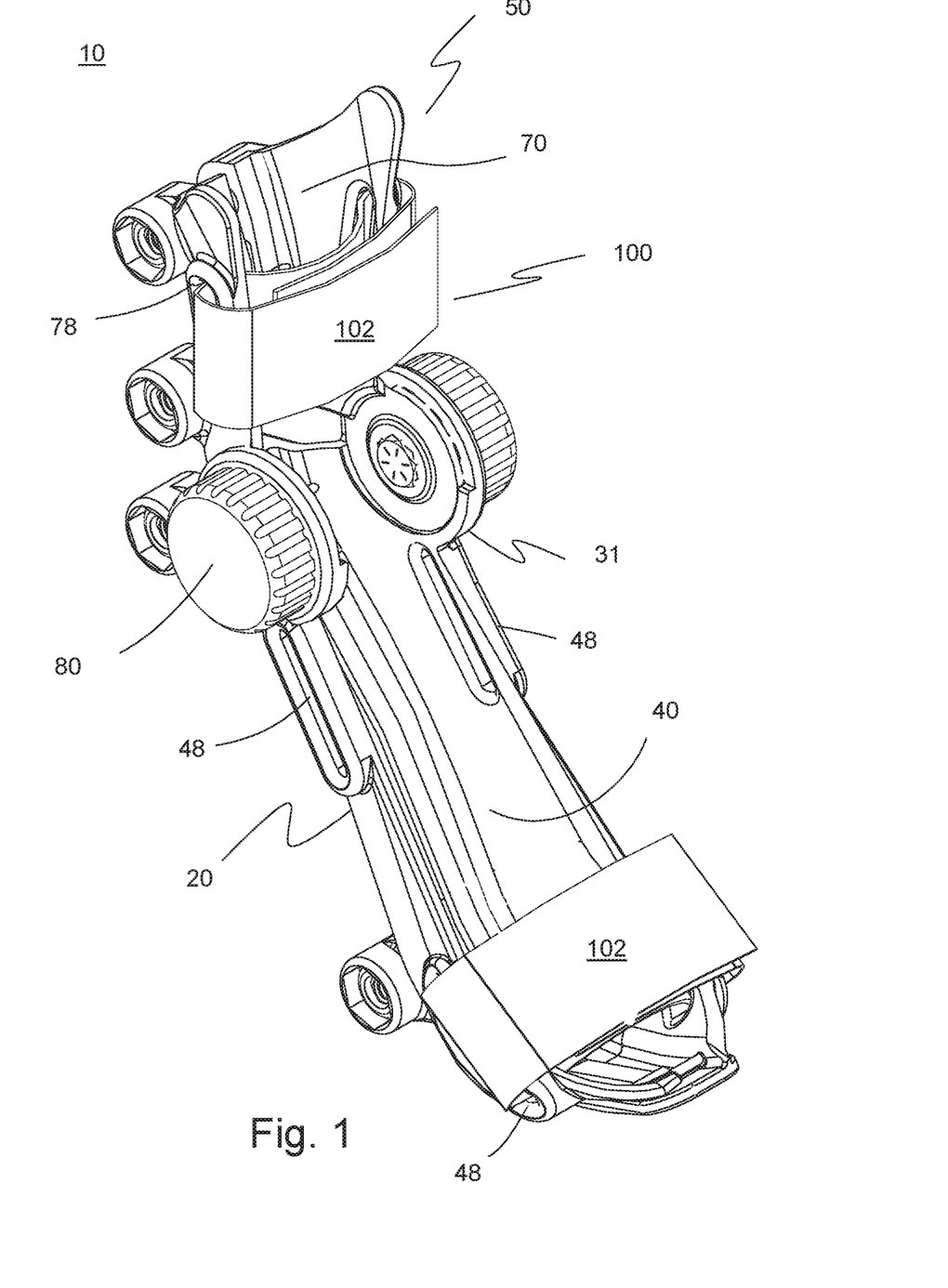
FIG. 1 is a front perspective view of one embodiment of the present invention showing an animal splint with retaining straps for an upper and lower leg with angle adjustment means.

Embodiments of the present invention are illustrated in FIGS. 1-11. FIG. 1 shows one embodiment of an animal splint 10 of the present invention. Animal splint 10 includes a lower leg assembly 20, an upper leg assembly 50, an angle fixing assembly 31, and a retaining means 100, which, in this embodiment, is a plurality of leg retaining straps 102. It is contemplated that any means for retaining animal splint 10 on a leg of a four-legged animal is included such as, for example, a continuous wrap around the leg and the splint, a tubular sock-like sleeve slid over the leg and the splint, tape, a plurality of straps that completely encircle the leg and the splint, a plurality of straps connected to animal splint 10 through a plurality of strap openings 48, 78, and the like. Animal splint 10 defines a lower leg trough-like space 40 in lower leg assembly 20 and an upper leg trough-like space 70 in upper leg assembly 50. Lower leg trough-like space 40 and upper leg trough-like space 70 are sized for receiving and immobilizing a leg of a four-legged animal.

Figure 2:
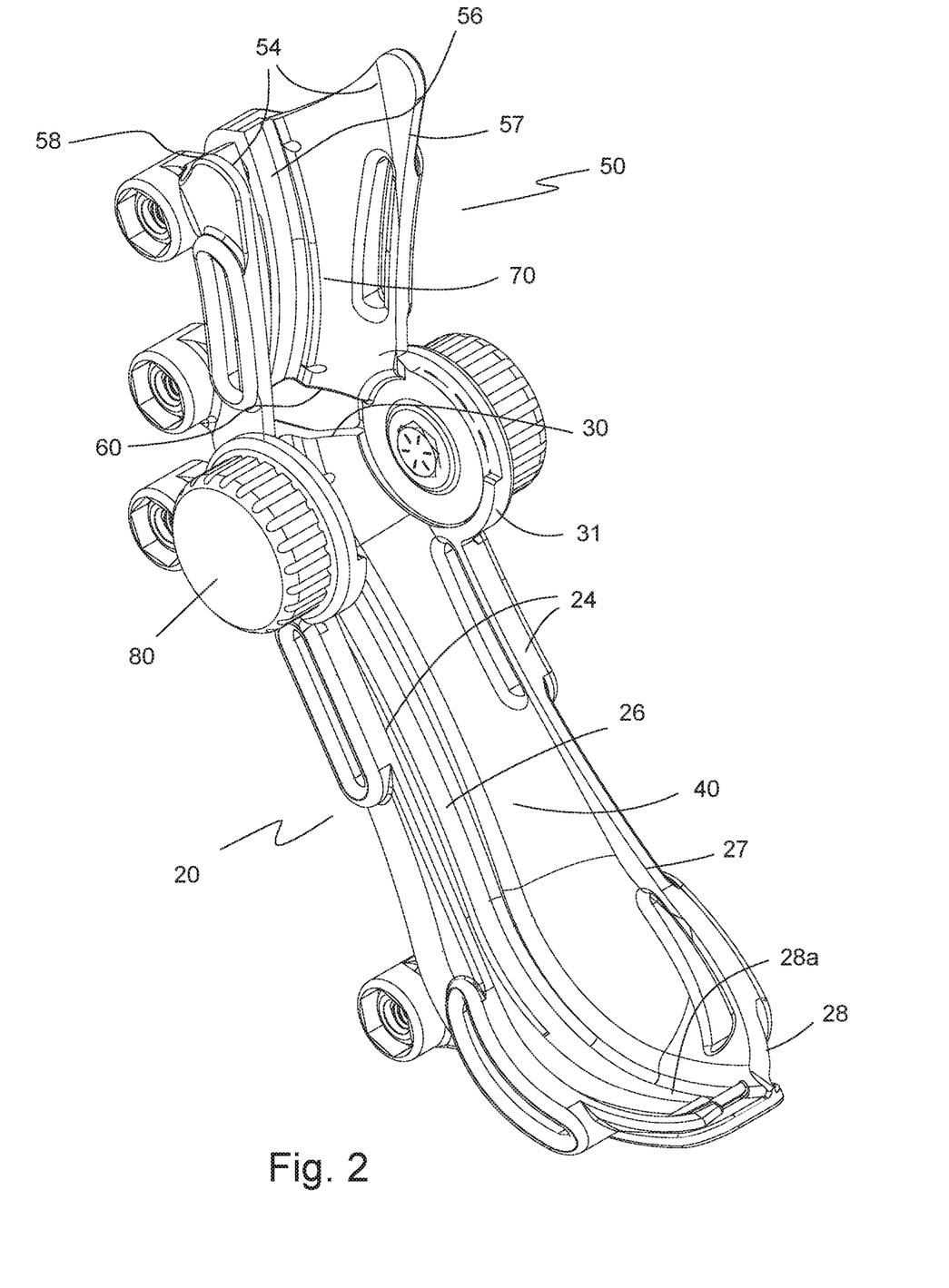
FIG. 2 is a perspective view of FIG. 1 without the retaining straps.

Turning now to FIG. 2, there is illustrated the embodiment shown in FIG. 1 with the retaining means 100 removed for clarity. Lower leg assembly 20 includes a pair of opposed sides 24, a lower leg back side 26 and an open front 27. Lower leg assembly also includes a distal foot portion 28 with a foot support surface 28a for supporting a paw of the leg of the four-legged animal, and a proximal lower leg portion 30. In this embodiment, angle fixing assembly 31 is adjacent proximal lower leg portion 30. Upper leg assembly 50 includes a pair of opposed sides 54, an upper leg back side 56 and an open front 57. Upper leg assembly 50 further includes a distal upper leg portion 58 and a proximal upper leg portion 60. Angle fixing assembly 31 is also adjacent proximal upper leg portion 60. Angle fixing assembly 31 allows a user to adjust the angle between open front 27 of lower leg assembly 20 and open front 57 of upper leg assembly 50 in order to fit animal splint 10 properly to a leg of a four-legged animal.

Figure 3:
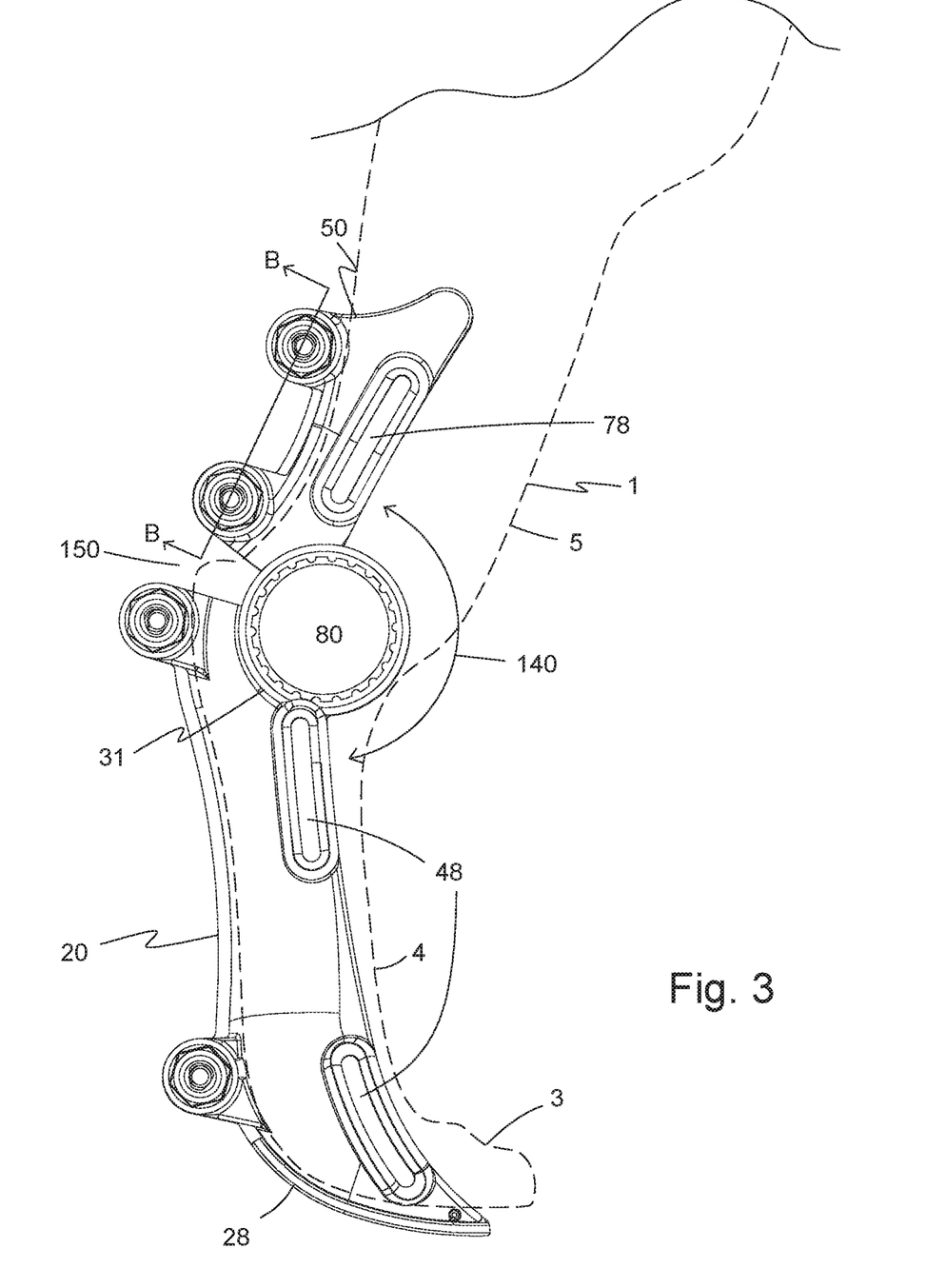
FIG. 3 is a side plan view of the animal splint of FIG. 1 showing the splint attached to an animal leg.

FIG. 3 is a plan side view of animal splint 10 with retaining means 100 removed for clarity. Animal splint 10 is shown positioned onto an animal leg 1 with animal leg 1 disposed within trough-like space 40 of lower leg assembly 20 and within trough-like space 70 of upper leg assembly 50. The animal foot 3 is disposed within distal foot support portion 28 while the animal leg joint 2 is disposed within animal splint 10 so that the "knee/elbow" is disposed in a space 150 between upper and lower leg assemblies 50, 20. Angle fixing assembly 31 is manipulated using adjustment member 80 to provide the proper angle 140 between lower and upper leg assemblies 20, 50 so that the animal lower leg 4 and the animal upper leg 5 are held in a natural and an immobilized position to promote healing of animal leg 1. Specifically, to enable this manipulation, first the adjustment member 80 is sufficiently loosened to allow rotation of first angle fixing member 32 relative to second angle fixing member 62 to align lower leg back side 26 with the rear of animal lower leg 4 and to align upper leg back side 56 with the rear of animal upper leg 5. After loosening, manipulating, rotating, and upon aligning the proper angular fit of animal splint 10 to animal leg 1, then retaining means 100 is manipulated to secure animal splint 10 onto animal leg 1. In this illustrated example, retaining straps (not shown) would be looped and/or connected to strap openings 48, 78 across the respective portion of animal leg 1 to maintain animal leg 1 securely within animal splint 10. Clearly, the advantage of having adjustment member 80 is the ability to adjust the angle between the lower and upper leg assemblies 20, 50 for proper fit to the angle between an animal's lower and upper leg 4, 5.

Figures 4, 5:
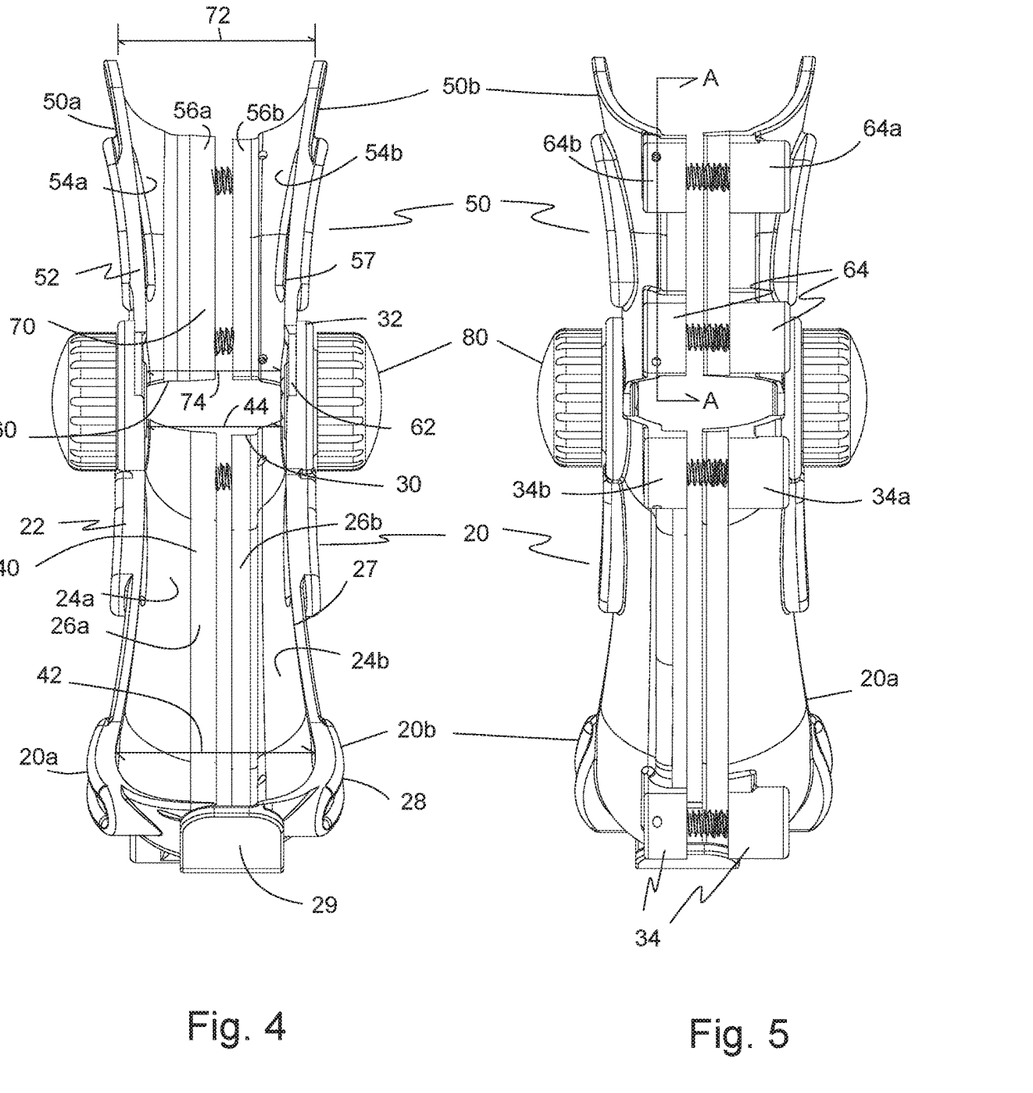
FIG. 4 is a front elevation view of the animal splint of FIG. 2.
FIG. 5 is a rear elevation view of the animal splint of FIG. 2.

FIG. 4 illustrates a front view of animal splint 10 shown in FIGS. 2-3. In this embodiment, lower leg assembly 20 includes a first lower leg member 20a and a second lower leg member 20b that is fastened to first lower leg member 20a. First lower leg member 20a has a first lower leg side 24a and a first lower back side portion 26a. Second lower leg member 20b has a second lower leg side 24b and a second lower back side portion 26b. When assembled to each other, first lower leg member 20a and second lower leg member 20b define a lower leg elongated body 22 with lower leg open front 27 and trough-like space 40. Trough-like space 40 has a cross-sectional area 42 at distal foot support portion 28 that is larger than the cross-sectional area 44 at proximal lower leg portion 30. As can be seen in this embodiment, distal foot support portion 28 has foot support member 29 formed or attached to lower leg assembly 20. Foot support member 29 may be formed with lower leg assembly 20 or with second lower leg member 20b as a single unit, as the case may be, or as a separate component that is later attached to distal foot support portion 28.

Upper leg assembly 50 includes a first upper leg member 50a and a second upper leg member 50b that is fastened to first lower leg member 50a. First upper leg member 50a has a first upper leg side 54a and a first upper back side portion 56a. Second upper leg member 50b has a second upper leg side 54b and a second upper back side portion 56b. When assembled to each other, first upper leg member 50a and second upper leg member 50b define an upper leg elongated body 52 with an upper leg open front 57 and trough-like space 70. Trough-like space 70 has a cross-sectional area 72 at distal upper leg portion 58 that is larger than the cross-sectional area 74 at proximal upper leg portion 60. Lower and upper leg assemblies 20, 50 are joined together by the mating of first angle fixing member 32 to second angle fixing member 62 at a preselected angle.

FIG. 5 is a back elevation view of the embodiment of animal splint 10 shown in FIG. 4. As can be seen from this view, one or more leg fastener parts 34, 64 are aligned with each other and have a fastener 12 that holds first lower leg member 20a to second lower leg member 20b and a separate configuration of one or more leg fastener parts 34, 64 that holds first upper leg member 50a to second upper leg member 50b. Lower leg fastener part 34 includes a first lower leg fastener bracket 34a secured to, or integrally formed with, or unitarily formed with first lower leg member 20a and a second lower leg fastener bracket 34b secured to, or integrally formed with, or unitarily formed with second lower leg member 20b. Upper leg fastener part 64 includes a first upper leg fastener bracket 64a secured to, or integrally formed with, or unitarily formed with first upper leg member 64a and a second upper leg fastener bracket 64b secured to, or integrally formed with, or unitarily formed with second upper leg member 64b. There are several advantages associated with animal splint 10 having first and second lower leg members 20a, 20b and first and second upper leg members 64a, 64b. The advantages include the ability to adjust the width of animal splint 10 for the size of the animal's leg being received in splint 10. Another advantage is that splint 10 covers more than 50% around the injured leg of the animal such as a dog compared to those that are shaped like half shells.

It is contemplated that when lower leg assembly 20 and/or upper leg assembly 50 is a single, unitary component, then such leg assembly would not have leg fastener parts 34, 64 because of the single unitary component configuration. In other words, there would be only one part that forms the leg assembly and, therefore, there would be no need for any leg fastener parts 34, 64.

Figure 6:
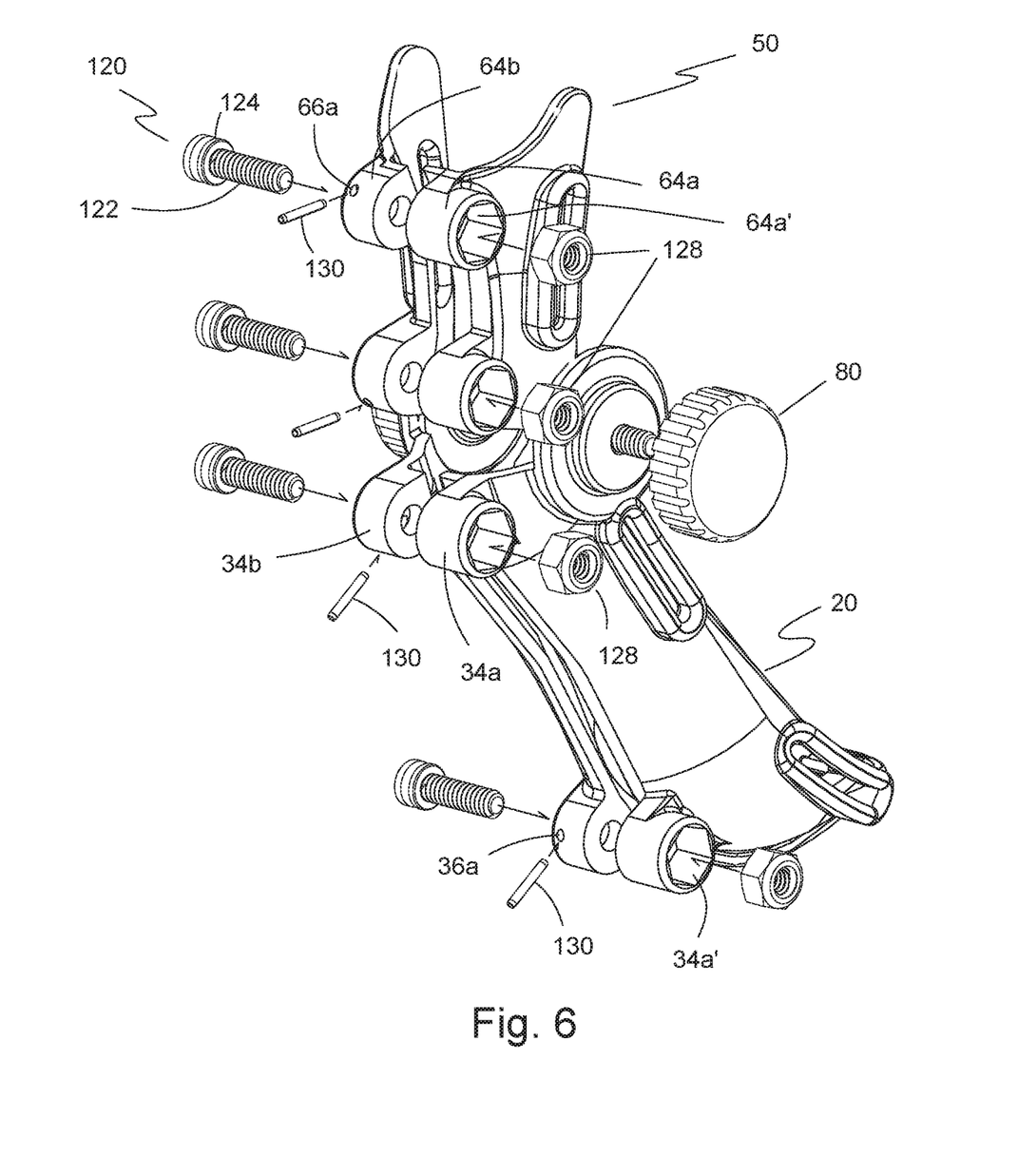
FIG. 6 is a rear perspective view of the animal splint of FIG. 2 showing the adjustment member and the leg assembly fasteners exploded.

FIG. 6 is a rear perspective view of animal splint 10 showing fastener 120 explode from leg fastener parts 34, 64. In this embodiment, fastener 120 includes a bolt 122 having a bolt head 124 and a nut 128. As indicated by the arrows, bolt 122 is disposed through first lower and upper leg fastener brackets 34b, 64b such that bolt head 124 resides within one of a bolt head recess 34b', 64b' (not shown) and extends into a respective second lower and upper leg fastener brackets 34a, 64a. Nut 128 is disposed into and resides within one of a nut recess 34a', 64a' and receives bolt 122 in threaded engagement. Nut recess 34a', 64a' may optionally have a cross-sectional shape that is the same as the cross-sectional shape of nut 128 so that the nut is held stationary when bolt 122 is screwed into nut 128. Optionally, first lower and upper leg fastener brackets 34b, 64b may have a pin bore 36a, 66a transverse to bolt head recess 34b', 64b', respectively, where pin bore 36a, 66a is offset from a longitudinal axis of the respective bolt head recess but extends through a portion of a portion of the bolt head recesses. Optionally, a locking pin 130 is disposed within pin bore 36a, 66a after bolt head 124 is disposed within bolt head recess 34b', 64b'. It is understood that, when an optional pin bore and locking pin 130 are included in first lower and upper fastener brackets 34b, 64b, bolt head 124 must necessarily include a groove to accommodate locking pin 130. The advantage of including a pin bore and locking pin in such an embodiment is to prevent bolt 122 from being inadvertently or accidentally removed out of bolt head recess 34b', 64b', respectively. It should be further understood that neither first and second leg fastener parts 34, 64 may include bolt head recesses 34b', 64b' or nut recesses 34a', 64a' where bolt head 124 and nut 128 are outside of leg fastener parts 34, 64 where hand tools may be used to tighten nut 128 unto bolt 122 to hold and secure the respective first and second leg members to each other. As also shown, adjustment member 80 is exploded from angle fixing assembly 31, which is described in more detail below.

Figure 7:
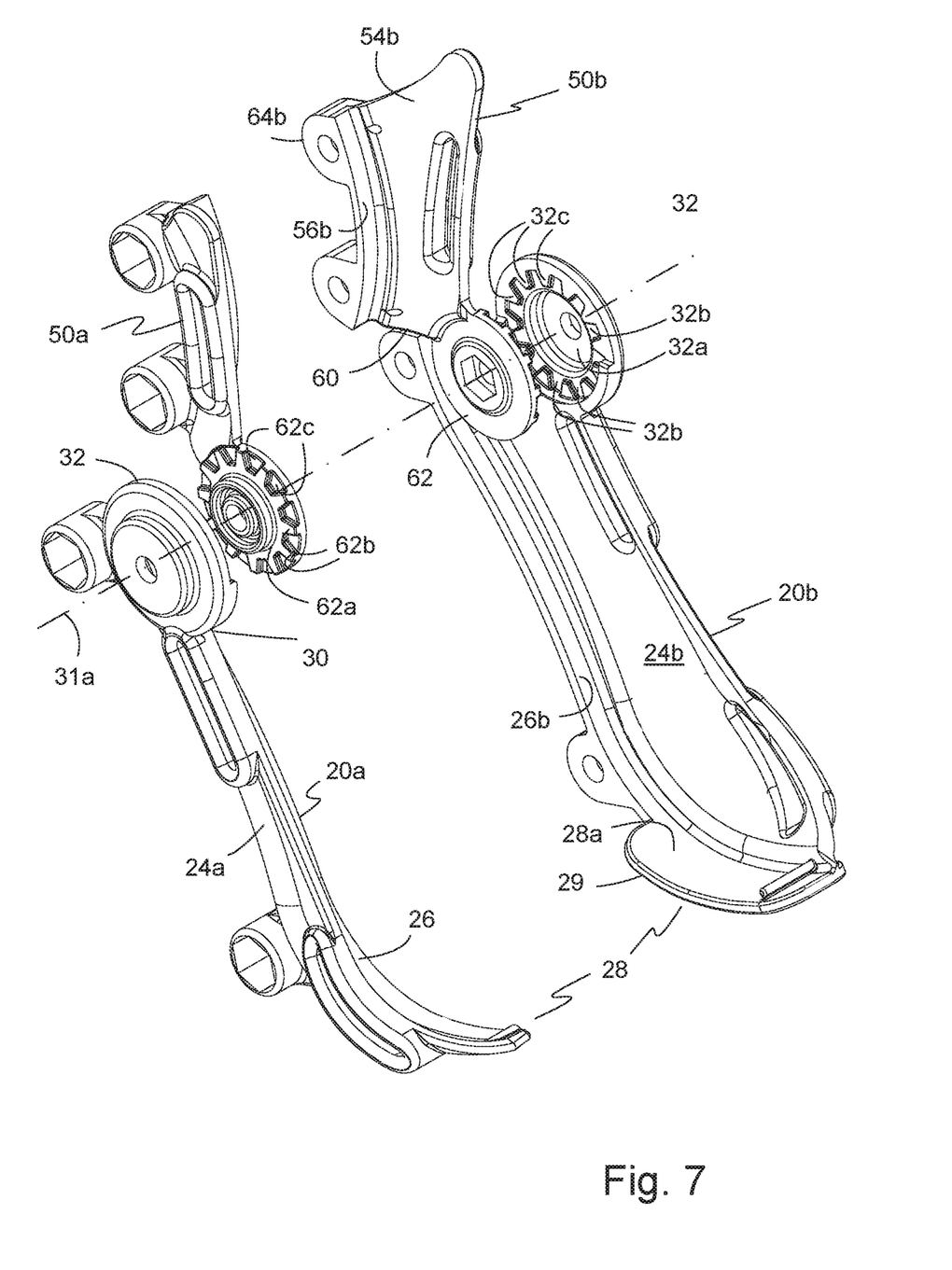
FIG. 7 is a front, right side perspective view of another embodiment of the present invention showing the lower leg assembly exploded from the upper leg assembly.
Figure 8:
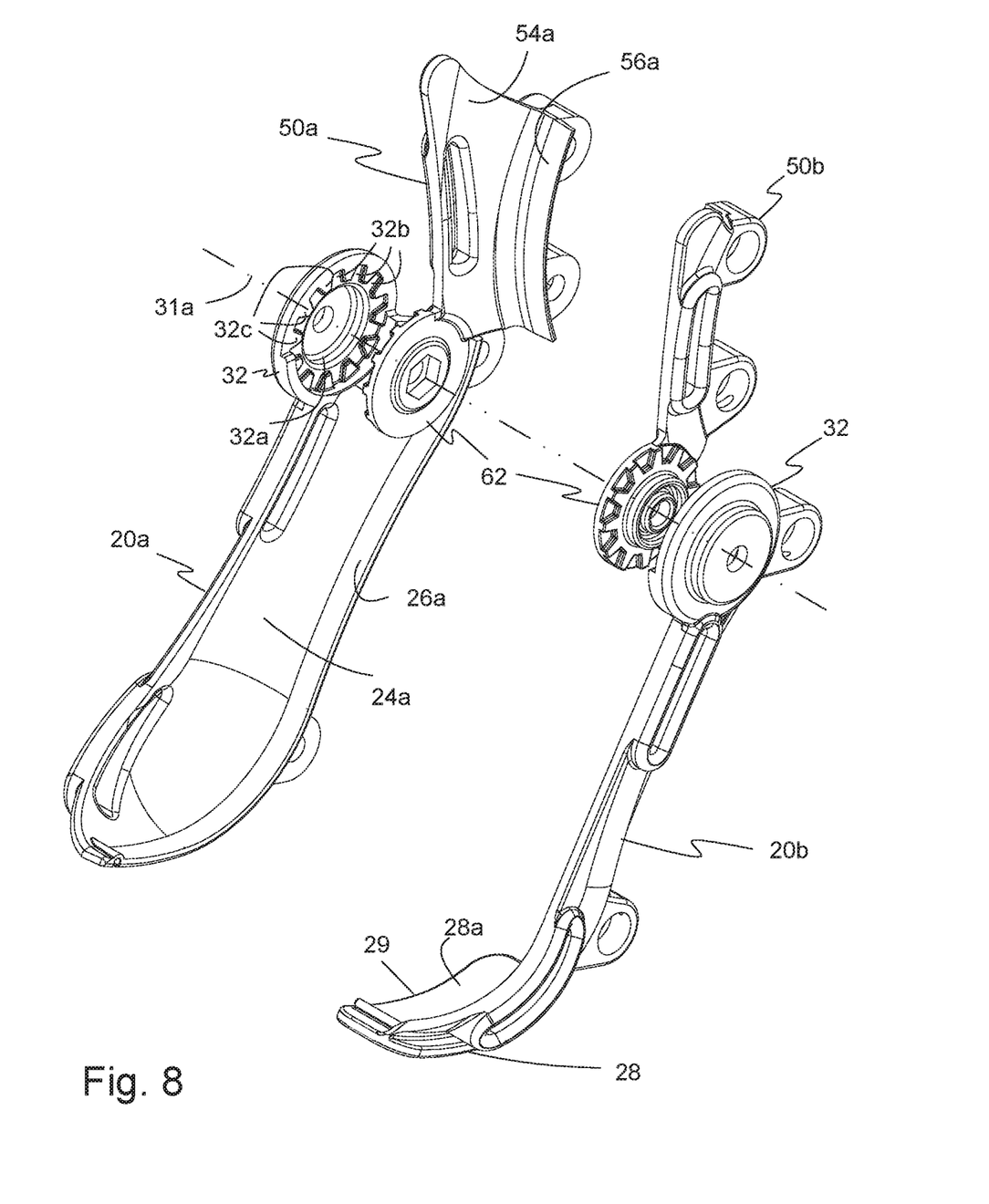
FIG. 8 is a front, left side perspective view of the embodiment in FIG. 7 showing the lower leg assembly exploded from the upper leg assembly.

Turning now to FIGS. 7 and 8, there is illustrated both front, right perspective, exploded view and front, left, perspective exploded view of one embodiment showing only lower leg assembly 20 and upper leg assembly 50. As shown in this embodiment, lower leg assembly 20 has first lower leg member 20a and second lower leg member 20b with respective first lower leg side 24a, first lower back side portion 26a, second lower leg side 24b, and second lower back side portion 26b. In addition, each of first and second lower leg members 20a, 20b has first angle fixing member 32 adjacent proximal lower leg portion 30. In this embodiment, first angle fixing member 32 is a gear-like recess 32a. Gear-like recess 32a has a circular shape with a plurality of alternating and equally-spaced, lower leg radial notch-like indents 32b directed radially and inwardly toward an angle fixing assembly axis 31a and forming a plurality of alternating and equally-spaced, lower leg radial teeth-like protrusions 32c.

Upper leg assembly 50 has first upper leg member 50a and second upper leg member 50b with respective first upper leg side 54a, first upper back side portion 56a, second upper leg side 54b, and second upper back side portion 56b. In addition, each of first and second upper leg members 50a, 50b has second angle fixing member 62 adjacent proximal upper leg portion 60. In this embodiment, second angle fixing member 62 is a gear-like protrusion 62a. Gear-like protrusion 62a has a circular shape with a plurality of alternating and equally-spaced, upper leg radial teeth-like protrusions 62b directed inwardly toward an angle fixing assembly axis 31a and forming a plurality of alternating and equally-spaced, upper leg radial notch-like indents 62c. The plurality of upper leg radial teeth-like protrusions 62b mate with the plurality of lower leg radial notch-like indents 32b and the plurality of upper leg radial notch-like indents 62c mate with the plurality of lower leg radial teeth-like protrusions 32c as an interlocking, angle fixing assembly 31. It is contemplated that the shape of the indents and protrusions may be any shape so long as the first and second angle fixing members 32, 62 can be brought together and joined along angle fixing assembly axis 31a where the indents and protrusions mate to interlock first angle fixing member 32 to second angle fixing member 62. It is also contemplated that the opposing surfaces of first and second angle fixing members 32, 62 may be frictional surfaces, keyed surfaces, or surfaces with a plurality of protuberances and mating sockets, and the like.

Figure 9:
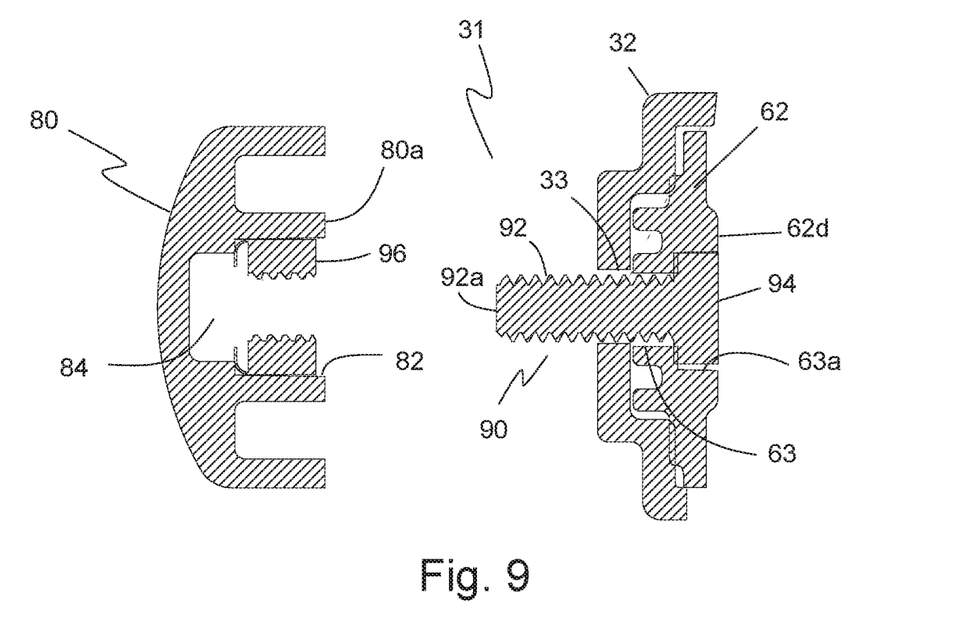
FIG. 9 is a cross-sectional and partially exploded view of one embodiment of the adjustment member showing the angle fixing bolt and nut relative to an angle fixing member assembly and the adjustment member.
Figure 9A:
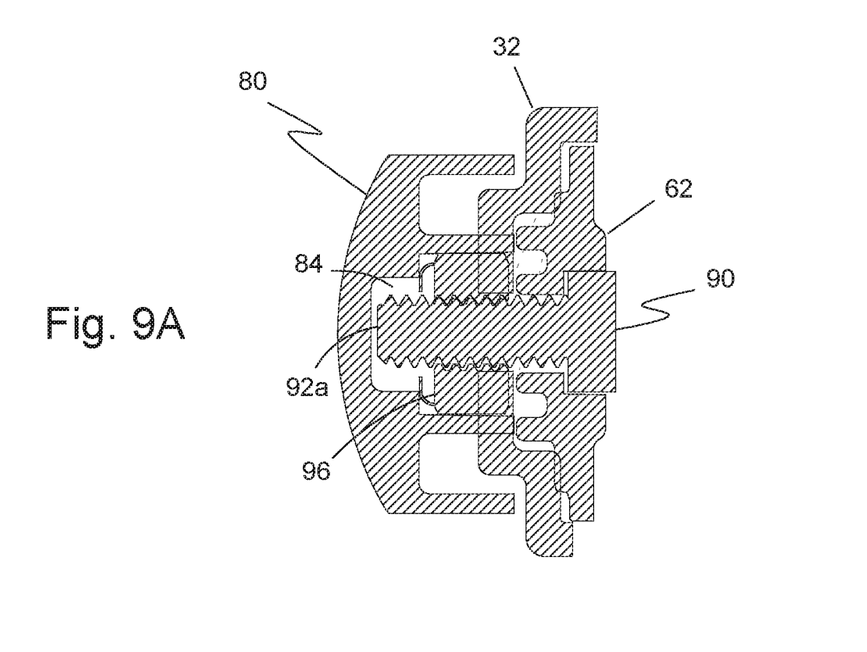
FIG. 9A is a cross-sectional view of FIG. 9 showing the adjustment member secured to the angle fixing fastener.

FIGS. 9 and 9A are cross-sectional views of angle fixing assembly 31 and adjustment member 80 of the embodiment shown in FIGS. 1-2. In this embodiment, angle fixing assembly 31 includes first angle fixing member 32, second angle fixing member 62, an angle fixing bolt 90 having a fixing bolt body 92 and a fixing bolt head 94, and an angle fixing nut 96. Angle fixing bolt 90 is disposed through first angle fixing member 32 and second angle fixing member 62. Specifically, second angle fixing member 62 has a second member bolt opening 63 that extends transversely completely through second angle fixing member 62 and a bolt-head recess 63a concentric with second member bolt opening 63. Bolt-head recess 63a extends from an inside surface 62d of second angle fixing member 62 a predefined distance sufficient for receiving fixing bolt head 94. First angle fixing member 32 has a first member bolt opening 33 that extends transversely completely through first angle fixing member 32, which is aligned and concentric with second member bolt opening 63. Fixing bolt body 92 extends completely through first and second angle fixing members 32, 62 and extends a predefined distance beyond first angle fixing member 32 for coupling with angle fixing nut 96.

Adjustment member 80 has a first recess 82 that extends axially into adjustment member 80 from an adjustment member inside surface 80a a predefined distance and having a cross-sectional area sufficient to receive and accommodate angle fixing nut 96. Adjustment member 80 also includes a second recess 84 that extends axially into adjustment member 80 from first recess 82 a predefined distance and having a cross-sectional area smaller that the cross-sectional area of first recess 82 but large enough to accommodate an end 92a of fixing bolt body 92.

Although first recess 82 of adjustment member 80 and bolt-head recess 63a may be circularly shaped to accommodate fixing bolt nut 96 and fixing bolt head 94, respectively, it is more convenient to form both first recess 82 and bolt-head recess 63a to have cross-sectional shapes that coincide with the cross-sectional shapes of fixing bolt nut 96 and fixing bolt head 94, respectively. This design eliminates the need to use hand tools for tightening fixing bolt nut 96 onto fixing bolt body 92 since the shaped first recess 82 and bolt-head recess 63a prevent rotation of the respective fixing bolt nut 96 and fixing bolt 90 during the assembly of adjustment member 80, first angle fixing member 32 and second angle fixing member 62.

Figure 10:
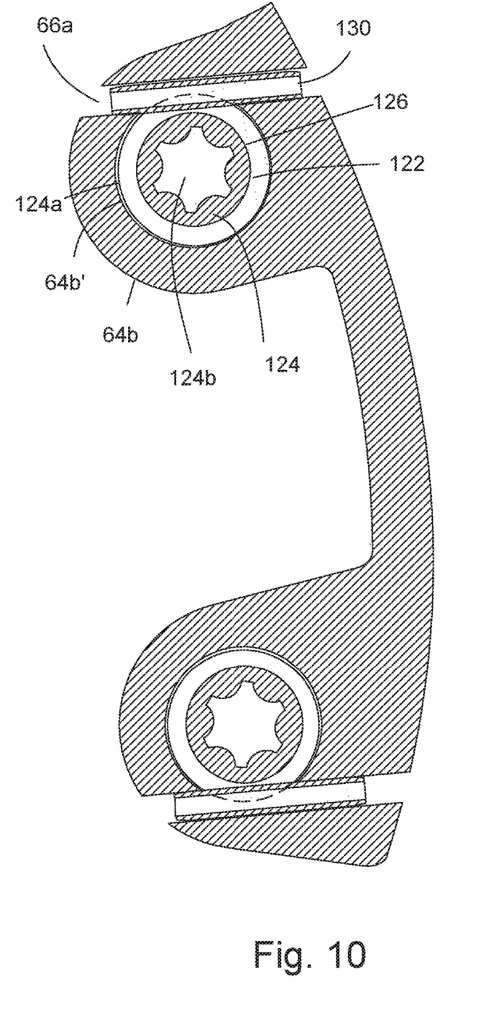
FIG. 10 is a cross-sectional view of one embodiment of a fastener part of the present invention taken along line A-A in FIG. 5 showing a pin bore with pin and fastener head assembled within the fastener part.

FIG. 10 is a cross-sectional view of leg fastener bracket 64a taken along lines B-B shown in FIG. 5. In this embodiment, bolt head 124 of fastener 120 is disposed within bolt head recess 64b' and bolt head 124 has a circumferential groove 126 around an outside, circumferential surface 124a of bolt head 124. Pin 130 is positioned within pin bore 66a, which passes through a portion of circumferential groove 126 to thereby lock bolt head 124 within head recess 64b'. A spring pin or split pin is one example of a usable pin for pin 130. In this embodiment, bolt head 124 is circular with a tool slot/recess 124b for receiving a star-type tool such as a star-shape tool sold under the trademark Torz®. It is contemplated that tool slot/recess 124b may be shaped for receiving other types of tools; the shapes include slotted, phillips, quadrex, square, hex, tri-wing, and spanner, all as is well-known in the art.

Figure 11:
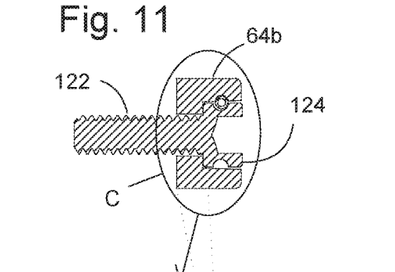
FIG. 11 is a cross-sectional view of the fastener part taken along line B-B in FIG. 3 showing the pin bore with pin and the fastener head of FIG. 10.
Figure 11A:
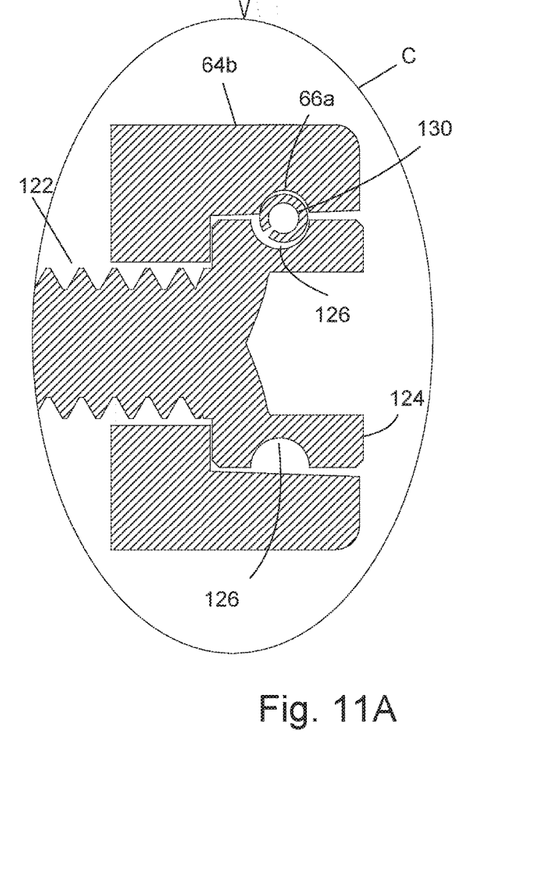
FIG. 11A is an enlarge view of the section indicated in FIG. 10 showing the locking pin within the pin bore and bolt head recess.

FIG. 11 is a cross-sectional view of bolt 122 and first upper leg fastener bracket 64b and FIG. 11A is an enlarged view of the area surrounded by line C in FIG. 10. Both FIGS. 11 and 11A show pin 130 within pin bore 66a and circumferential groove 126 of bolt head 124. The advantage of the circumferential slot 126 in bolt head 124 is that bolt 122 is retained within first upper leg fastener bracket recess 64a' by pin 130. Yet, the bolt 122 can still be rotated to tighten or loosen bolt 122 into nut 128.

Animal splint 10 has advantages over prior art devices in that splint 10 is adjustable to fit various angles between an animal's rear upper and lower leg to more closely match the injured animal's leg as well as to fit various thicknesses of an animal's rear leg. A better fit of an animal splint helps promote healing of the injured leg as well as protecting the animal's leg from further injury.

Although the preferred embodiments of the present invention have been described herein, the above description is merely illustrative. Further modification of the invention herein disclosed will occur to those skilled in the respective arts and all such modifications are deemed to be within the scope of the invention as defined by the appended claims.

What is claimed is:

1. An animal splint for immobilizing a leg of an animal, the animal splint comprising:
   a lower leg assembly having:
      a lower leg elongated body, with a pair of lower leg members being disparate and distinct structures on opposed left and right sides of the lower leg elongated body, wherein together the pair of lower leg members forming the lower leg elongated body having a lower leg open back, a lower leg open front forming a lower leg trough shaped space, a distal foot support portion, and a proximal lower leg portion opposite the distal foot support portion;
      a first lower angle fixing member integrally formed in the proximal lower leg portion of a first of the pair of lower leg members;
      a second lower angle fixing member integrally formed in the proximal lower leg portion of a second of the pair of lower leg members;
      a lower leg retaining means extending across the lower leg open front for releasably retaining the animal splint to the leg of the animal;
      a lower fastener assembly positioned on the open back and having a pair of fastener brackets and a threaded fastener, each of the pair of fastener brackets being integrally formed with a respective one of the pair of lower leg members, each of the pair of fastener brackets projecting from their respective one of the pair of lower leg members and having a recess therein for accepting the threaded fastener, the threaded fastener reversibly and adjustably joining the pair of fastener brackets thereby facilitating the lower fastener assembly in extending across a gap defined by the open back and configured for adjusting a width of the trough shaped space at the lower leg open back;
      wherein the distal foot support portion of the lower elongated body is formed by a foot support member extending outward from one of the pair of lower leg members and extending under another of the pair of lower leg members so as to close the gap along the open back of the distal foot support portion;
   an upper leg assembly having:
      an upper leg elongated body with a pair of upper leg members being disparate and distinct structures on opposed left and right sides of the upper leg elongated body, wherein the pair of upper leg members forming the upper leg elongated body having an upper leg open back, an upper leg open front forming an upper leg trough shaped space, a distal upper leg portion, and a proximal upper leg portion opposite the distal upper leg portion;
      a first upper angle fixing member integrally formed in a distal lower leg portion of a first of the pair of upper leg members;
      a second upper angle fixing member integrally formed in a distal lower leg portion of a second of the pair of upper leg members; and
      an upper leg retaining means extending across the upper leg open front and connecting the pair of upper leg members for releasably retaining the animal splint to the leg of the animal;
      wherein the first and second upper angle fixing members are configured for mating engagement with the first and second lower angle fixing members respectively, such that the mating engagement facilitates angular adjustment between the lower leg assembly and the upper leg assembly;
   a first angular adjustment member further engaging the mated first upper and lower angle fixing members, the first angular adjustment member configured for releasably fixing the first upper angle fixing member of the upper leg assembly and the first lower angle fixing member of the lower leg assembly relative to each other; and
   a second angular adjustment member further engaging the mated second upper and lower angle fixing members, the second angular adjustment member configured for releasably fixing the second upper angle fixing member of the upper leg assembly and the second lower angle fixing member of the lower leg assembly relative to each other, whereby the first and the second angular adjustment members permit adjusting an angle between the lower leg assembly and the upper leg assembly, such that in cooperation with the leg retaining means, the leg of the animal is releasably retained and held in an immobilized position by the animal splint.

2. The animal splint of claim 1 wherein the lower leg assembly is longer than the upper leg assembly.

3. The animal splint of claim 1 wherein the first lower angle fixing member is a gear shaped recess integrally formed in the proximal leg portion of the first of the pair of lower leg members, such that the first lower angle fixing member has a circular shape with a plurality of alternating and equally-spaced, lower leg radial notch indents directed radially and inwardly toward an angle fixing assembly axis and forming a plurality of alternating and equally-spaced lower leg radial teeth protrusions.

4. The animal splint of claim 3 wherein the first upper angle fixing member is a complimentary gear shaped protrusion integrally formed in the distal leg portion of the first of the pair of upper leg members, such that the first upper angle fixing member has a circular shape with a plurality of alternating and equally-spaced, upper leg radial teeth protrusions directed inwardly toward an angle fixing assembly axis and forming a plurality of alternating and equally-spaced, upper leg radial notch indents.

5. The animal splint of claim 1 wherein the leg retaining means is a plurality of leg retaining straps connected to the lower leg assembly and the upper leg assembly whereby the plurality of leg retaining straps extends across the lower leg open front between the pair of lower leg members and the upper leg open front between the pair of upper leg members.

6. The animal splint of claim 1 wherein the pair of lower leg members includes the first lower leg member having a first lower leg side portion and a first lower back side portion, and the second lower leg member having a second lower leg side portion and a second lower back side portion; the gap along the open back extends widthwise between the first lower back side portion and the second lower back side portion; and the gap along the open back extends lengthwise from the distal foot support portion to the proximal lower leg portion opposite the distal foot support portion.

7. The animal splint of claim 1 wherein the pair of upper leg members includes the first upper leg member having a first upper leg side portion and a first upper back side portion, and the second upper leg member having a second upper leg side portion and a second upper back side portion; the gap along the open back extends widthwise between the first upper back side portion and the second upper back side portion; and the gap along the open back extends lengthwise from the distal upper leg portion to the proximal upper leg portion opposite the distal upper leg portion.

8. A method of using the animal splint of claim 1 to immobilize the leg of the animal, the method comprising:
   assembling the first and second lower angle fixing members of the lower leg assembly and the first and second upper angle fixing members of the upper leg assembly to each other at the angle defined by the animal's leg to be immobilized;
   attaching and tightening the first and second angular adjustment members to lock the angle between the lower leg assembly and the upper leg assembly;
   inserting a lower leg of the animal within the lower leg trough shaped space of the lower leg assembly;
   inserting an upper leg of the animal within the upper leg trough shaped space of the upper leg assembly;
   adjusting the width of the upper and lower backs of the of the upper and lower leg assemblies to correspond to a width of the lower leg and upper leg of the animal; and
   securing the animal splint on the leg of the animal using the leg retaining means.

9. The method of claim 8 further comprising assembling the first lower leg member to the second lower leg member before assembling the first lower angle fixing member to the first upper angle fixing member and the second lower angle fixing member to the second upper angle fixing member.

10. The method of claim 8 further comprising assembling the first upper leg member to the second upper leg member before assembling the first lower angle fixing member to the first upper angle fixing member and the second lower angle fixing member to the second upper angle fixing member.

11. An animal splint for immobilizing a leg of an animal, the animal splint comprising:
   an upper and a lower leg assembly, each having:
      an elongated body having a pair of members, the pair of members being disparate and distinct structures on opposed left and right sides, forming the elongated body having a trough shaped space with an open back, an open front, a distal portion, and a proximal portion;
      a cross-sectional area of the trough shaped space at one of the distal portion and proximal portion being larger than a cross-sectional area of the trough shaped space at the other of the one of the distal portion and proximal portion;
      a leg retaining strap for releasably retaining the animal splint to the leg of the animal, the leg retaining strap extending across the open front, and capable of facilitating a variable depth between the retaining strap at the open front and the open back; and
      a width fastener having a pair of fastener brackets connected by a corresponding threaded fastener, each of the pair of fastener brackets being integrally formed with a respective one of the pair of members, the width fastener extending across the open back and configured for a width of the open back, wherein the width of the open back corresponds to a gap which extends widthwise between the pair of members and fully lengthwise from the distal portion to the proximal portion; and
      a pair of angle fixing members, each of the pair of angle fixing members being integrally formed with a respective one of each of the pair of members;
   wherein the upper and lower leg assemblies are connected to one another by mating engagement of the pair of angle fixing members; and
   a pair of angle adjustment members further interacts with the matingly engaged pairs of angle fixing members of the upper and lower leg assemblies and thereby adjustably secures the pair of angle fixing members of the upper leg assembly and the pair of angle fixing members of the lower leg assembly at a specific fixed angle relative to each other.

* * * * *